(12) United States Patent
Aldridge et al.

(10) Patent No.: US 8,428,680 B2
(45) Date of Patent: Apr. 23, 2013

(54) HYBRID MULTICHANNEL PRINTED CIRCUIT BOARD MICRODRIVE

(75) Inventors: J. Wayne Aldridge, Ann Arbor, MI (US); Andrew Klein, Ann Arbor, MI (US); Marc Bradshaw, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 930 days.

(21) Appl. No.: 12/255,223

(22) Filed: Oct. 21, 2008

(65) Prior Publication Data

US 2009/0105776 A1    Apr. 23, 2009

Related U.S. Application Data

(60) Provisional application No. 60/981,579, filed on Oct. 22, 2007.

(51) Int. Cl.
*A61N 1/00* (2006.01)
*A61B 5/04* (2006.01)

(52) U.S. Cl.
USPC .......... 600/378; 607/2; 607/45; 607/115; 607/116; 600/372; 600/377; 600/383; 600/386; 600/544

(58) Field of Classification Search .......... 600/372, 600/377, 378, 382, 383, 386, 544, 545; 607/1, 607/2, 45, 56, 57, 115–118, 148
See application file for complete search history.

(56) References Cited

U.S. PATENT DOCUMENTS

| | | | |
|---|---|---|---|
| 5,951,323 A | 9/1999 | Hofmann et al. | |
| 6,249,691 B1 | 6/2001 | Pezaris et al. | |
| 7,769,421 B1 * | 8/2010 | Stengel et al. | 600/378 |
| 2006/0095105 A1 * | 5/2006 | Jog et al. | 607/116 |
| 2006/0282014 A1 | 12/2006 | Kipke et al. | |

OTHER PUBLICATIONS

A New Electrical Recording Neural Probe Integrated with Chemical Stimulation; The 13th International Conference on Solid-State Sensors, Actuators and Microsystems, Seoul, Korea, Jun. 5-9, 2005; pp. 1808-1811.
A New Neural Probe Using SOI Wafers with Topological Interlocking Mechanisms; 1st Annual International IEEE-EMBS Special Topic Conference on Microtechnologies in Medicine & Biology Oct. 12-14, 2000, Lyon, France; Poster 89; pp. 507-511.
Appendix 1: Miniature Motorized Microdrive Construction Protocol; pp. 71-81.

(Continued)

*Primary Examiner* — Niketa Patel
*Assistant Examiner* — Lindsey G Hankins
(74) *Attorney, Agent, or Firm* — Howard & Howard Attorneys PLLC

(57) ABSTRACT

A miniature microdrive system may be affixed to the skull and used to advance recording electrode bundles or injection cannula through the brain of freely moving test subjects, e.g., rodents. The microdrive may be constructed using a hybrid fabrication technique utilizing a printed circuit board and a small number of mechanical parts. The printed circuit board provides the base for both the electrical components and the mechanical components. The movement of a screw advances a shuttle that in turn moves an electrode bundle through the brain. Independently moving screws advance independent electrode bundles. The electrode wires are connected through the printed circuit board to a connector on the back of the board. Stainless steel cannulae are soldered to a grounding trace on the printed circuit board to guide the electrode bundle and provide a ground connection. With this system, multiple brain structures may be targeted simultaneously. The microdrive system or device is simple to mass produce, making fabrication simple with parts that can be recycled or discarded as needed.

24 Claims, 7 Drawing Sheets

OTHER PUBLICATIONS

Miniature Motorized Microdrive and Commutator System for Chronic Neural Recording in Small Animals; by Michale S. Fee; Journal of Neuroscience Methods 112 (2001) pp. 83-94.

The Application of Printed Circuit Board Technology for Fabrication of Multi-Channel Micro-Drives; by Imre Szabo et al; Journal of Neuroscience Methods 105 (2001) pp. 105-110.

* cited by examiner

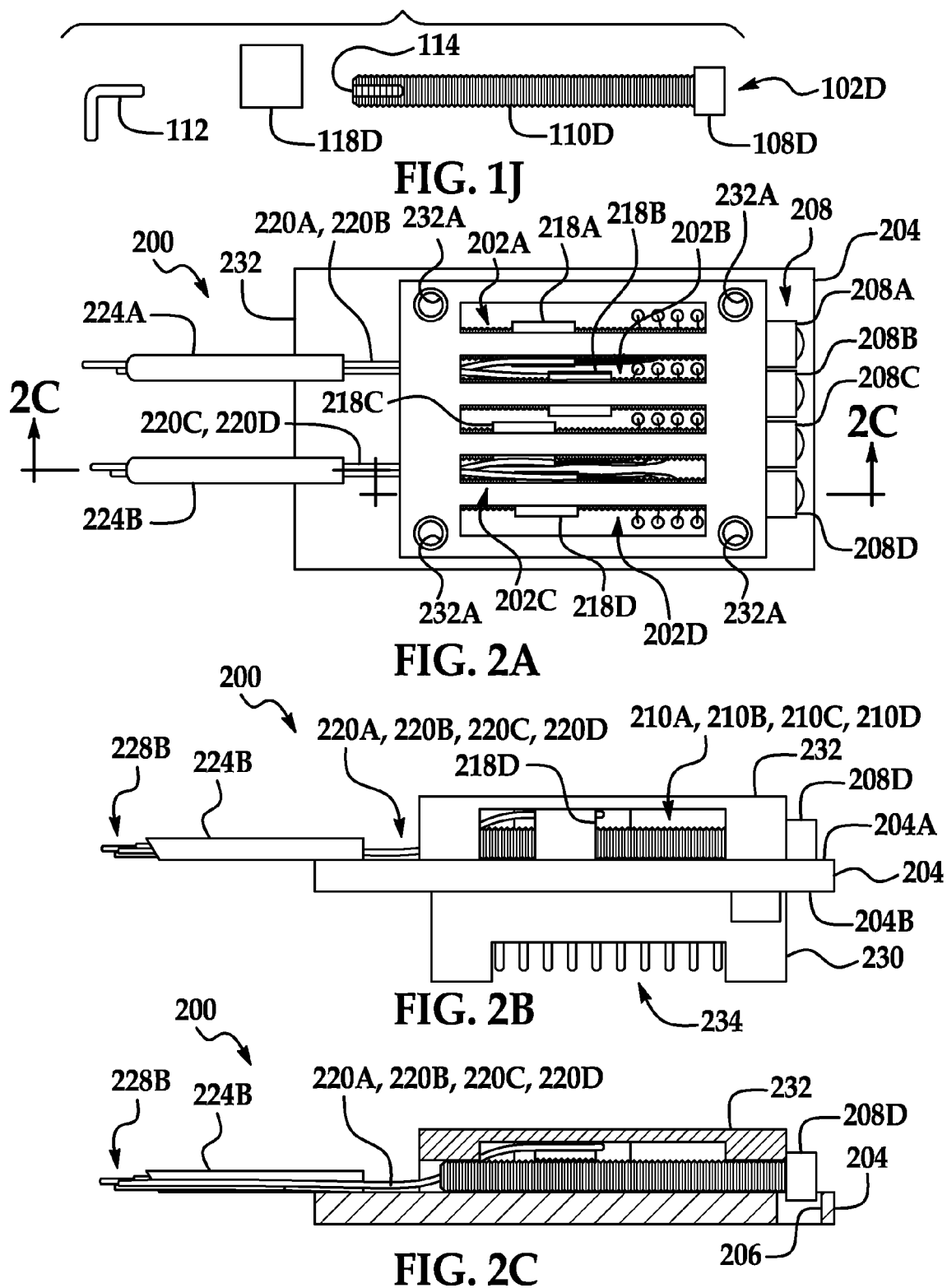

HYBRID MULTICHANNEL PRINTED CIRCUIT BOARD MICRODRIVE

CROSS REFERENCE TO RELATED APPLICATION

The present application claims priority to U.S. Provisional Patent Application Ser. No. 60/981,579, filed Oct. 22, 2007, which is hereby incorporated by reference in its entirety.

GOVERNMENT LICENSE RIGHTS

This invention was made with government support under DA017752, awarded by the National Institutes of Health. The government has certain rights in the invention.

FIELD OF THE INVENTION

The present invention relates generally to an integrated implanted cannula, microdrive, electrodes and electrode system, and more particularly, to a system which integrates a miniature microdrive and electrodes (or injection cannula) into a single package on a printed circuit board.

BACKGROUND OF THE INVENTION

The ability to probe multiple sites with the brain of a test subject, such as rodents or birds, simultaneously holds much potential in the biomedical field, especially for understanding the relationship between neuronal patterns and behavior.

The use of portable devices or systems which may be affixed to the test subject with microdrives for placement of the one or more electrodes has been known.

For example, two such systems are shown in:

1. Szabó, I, Czurkó, A, Csicsvari, J, Hirase, J, Leinekugal, X, Buszáki, G. The application of printed circuit board technology for fabrication of multi-channel micro-drives. Journal of Neuroscience Methods 105 (2001) 105-110.

2. Fee, M, Leonardo, A. Miniature motorized microdrive and commutator system for chronic recording in small animals. Journal of Neuroscience Methods 112 (2001) 83-94.

The Szabó reference discloses a micro-drive system. Not including the motors, these systems typically include three main components: (1) the microdrives, which typically include one or more micro-screws, (2) the electrodes, and (3) the electrical connectors for connecting the electrodes to off-system electronics for recording the signals from the electrodes.

As best can be seen in FIG. 5 of Szabó, the Szabó system includes 8 micro screws mounted between two parallel mounting boards. The micro screws drive individual electrodes which are fed through a separate member which is coupled to the mounting boards via a frame comprised of three framing members which are soldered to. The electrodes are electrically coupled to a connector which is mounted on a separate connector board. The connector board is affixed to the mounting boards via four additional framing members. As can be easily seen, the Szabó system is complex, made up a multitude of parts, which must be assembled in a complex, time consuming process. Furthermore, the three separate components are connected together via various framing members, which require frequent adjustment and repair.

As best can be seen in FIG. 3 of Fee, the Fee system also separates out the 3 main components of the system which each must be separately assembled and then assembled into a single unit, making the Fee system also difficult and time consuming to assembly and prone to breaking, requiring frequent repairs and adjustments.

The present invention is aimed at one or more of the following problems identified above.

SUMMARY OF THE INVENTION

In a first aspect of the present invention, an integrated microdrive and electrode system or device is provided. The microdrive includes one or more drive screws which may be adjusted manually or via a motor. The device may include a single or unitary base. The device positions and holds each screw in a position parallel to the board while allowing the screws to turn freely. The device includes a threaded shuttle which rides a respective screw. Movement of the shuttles advances/withdraws a respective electrode through a fixed cannulae, which is fixed to the board.

In a second aspect of the present invention, one or more of the components of the devices may be unitarily formed.

In a third aspect of the present invention, an apparatus having a base, a retaining bracket, a micro-screw, a cannula, a shuttle, and an electrode is provided. The base has a first surface and a second surface and a first end and a second end. The retaining bracket is mounted to the first surface of the base near the first end and has a bore parallel to a plane of the base. The micro-screw has a head and a shaft and is located within the bore. The head defines a shoulder which rests against one side of the retaining bracket. The shaft is threaded and extends through the bore towards the second end. The micro-screw is held along, and rotatable about, an axis parallel to the base, by the retaining bracket. The cannula has an internal bore and is mounted to the first surface. The shuttle has a bore with internal threads which are in a coupling relationship with the threads of the micro-screw. The micro-screw is rotatable in a first rotary direction causing the shuttle to be advanced along the micro-screw in a first direction and in a second rotary direction causing the shuttle to be advanced along the micro-screw in a second direction. The electrode has a first end and a second end and is coupled to the shuttle. The second end of the electrode is threaded through the cannula such that motion of the shuttle along the micro-screw moves the electrode through the cannula.

In a fourth aspect of the present invention, an apparatus having a base, a retaining bracket, first and second micro-screws, a first cannula, a second cannula, first and second shuttles, and first and second electrodes is provided. The base has a first surface and a second surface and a first end and a second end. The retaining bracket is mounted to the first surface of the base near the first end and has a bore parallel to a plane of the base. The first micro-screw has a head and a shaft and is located within the bore. The head defines a shoulder which rests against one side of the retaining bracket. The shaft is threaded and extends through the bore towards the second end. The first micro-screw is held along, and rotatable about, an axis parallel to the base, by the retaining bracket. The first cannula has an internal bore and is mounted to the first surface. The first shuttle has a bore with internal threads which are in a coupling relationship with the threads of the first micro-screw. The first micro-screw is rotatable in a first rotary direction causing the shuttle to be advanced along the first micro-screw in a first direction and in a second rotary direction causing the shuttle to be advanced along the first micro-screw in a second direction. The first electrode has a first end and a second end and is coupled to the first shuttle. The second end of the first electrode is threaded through the first cannula such that motion of the first shuttle along the first micro-screw moves the electrode through the first cannula.

The second micro-screw has a head and a shaft and is located within a second bore of the retaining bracket. The head of the second micro-screw defines a shoulder which rests against the one side of the retaining bracket. The shaft of the second micro-screw is threaded and extends through the second bore towards the second end. The second micro-screw is held along, and rotatable about, the axis parallel to the base, by the retaining bracket. The second cannula has an internal bore and is mounted to the first surface. The second shuttle has a bore with internal threads which are in a coupling relationship with the threads of the second micro-screw. The second micro-screw is rotatable in the first rotary direction causing the second shuttle to be advanced along the second micro-screw in the first direction and in the second rotary direction causing the second shuttle to be advanced along the second micro-screw in the second direction. The second electrode has a first end and a second end and is coupled to the second shuttle. The second end of the second electrode is threaded through the second cannula such that motion of the second shuttle along the second micro-screw moves the second electrode through the second cannula.

BRIEF DESCRIPTION OF THE DRAWINGS

Other advantages of the present invention will be readily appreciated as the same becomes better understood by reference to the following detailed description when considered in connection with the accompanying drawings wherein:

FIG. 1J is a view of a securing hook, a shuttle, and a micro-screw of the system of FIG. 1A;

FIG. 2A is a top view of an integrated micro drive and electrode system, according to another embodiment of the present invention;

FIG. 2B is a side view of the system of FIG. 2A;

FIG. 2C is a cut away of the system of FIG. 2A;

DETAILED DESCRIPTION OF INVENTION

Figure 1A:
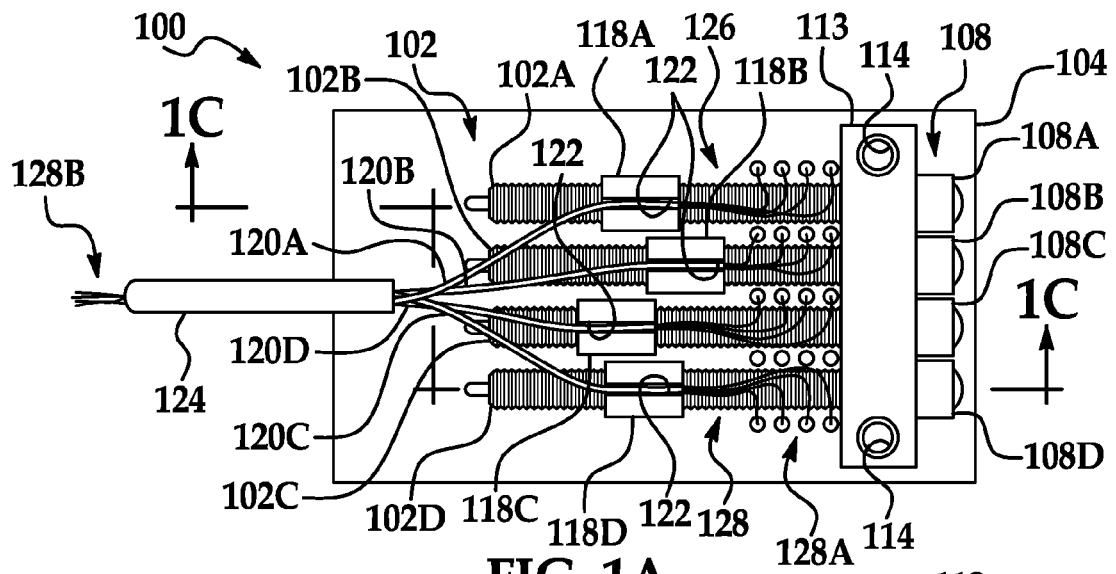
FIG. 1A is a top view of an integrated micro drive and electrode system, according to an embodiment of the present invention.
Figure 1B:
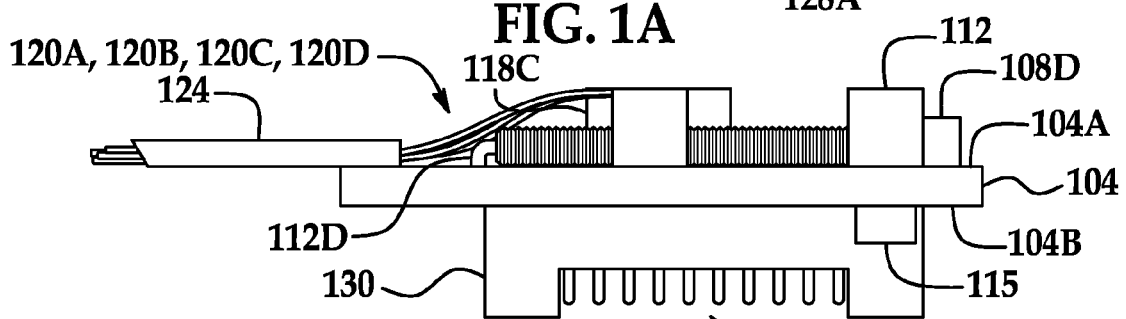
FIG. 1B is a side view of the system of FIG. 1A.
Figure 1C:
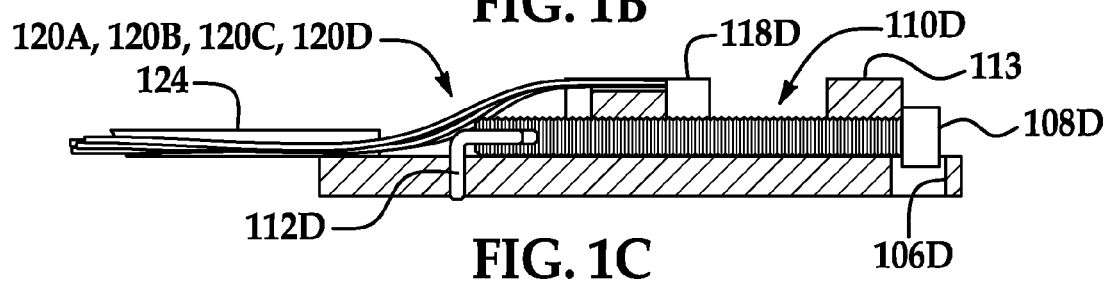
FIG. 1C is a cut away of the system of FIG. 1A.
Figure 1D:
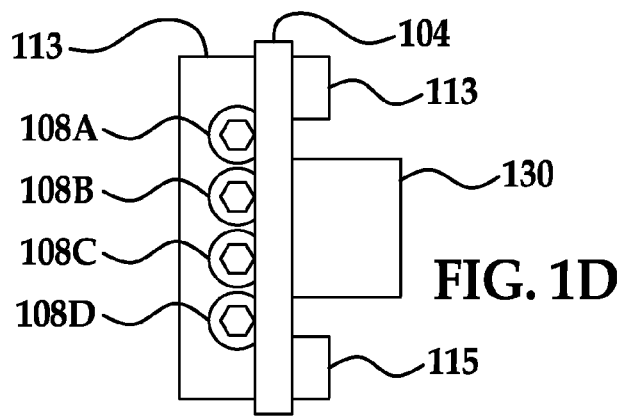
FIG. 1D is an end view of the system of FIG. 1A.
Figure 1E:
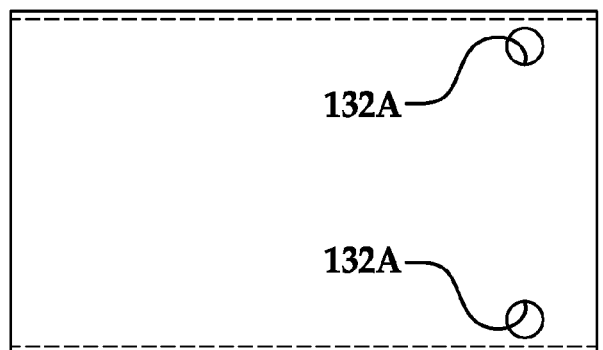
FIG. 1E is a top view of a cover of the system of FIG. 1A.
Figure 1F:
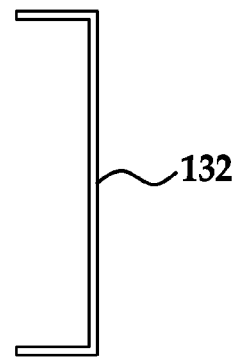
FIG. 1F is an end view of the cover of FIG. 1E.
Figure 1G:
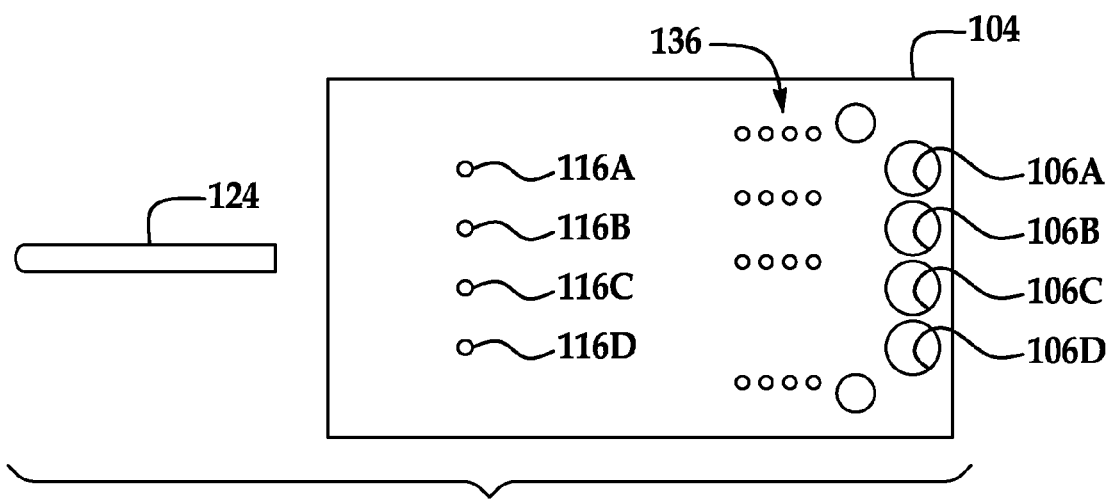
FIG. 1G is a component view of several components of the system of FIG. 1A.
Figure 1H:
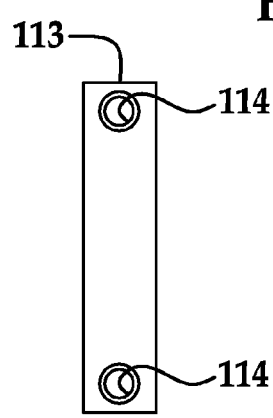
FIG. 1H is a first view of a screw retainer.
Figure 1I:
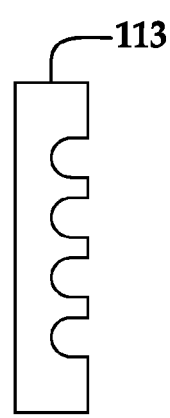
FIG. 1I is a second view of the screw retainer.

Referring to the Figures, wherein like numerals indicate like or corresponding parts throughout the several views, the present invention provides an integrated microdrive and electrode system or device 100, 200, 300 which is capable of advancing independent electrodes for the independent recording at multiple sites within the brain of test subjects, e.g., rodents, birds, etc. . . . .

The integrated device 100, 200, 300 may be affixed outside the skull of the subject with the electrodes inserted or implanted through the skull and into the brain of the subject. As discussed below, the micro-drive may include one or more micro-screws 102, 202, 302, which may be adjusted either manually or via a motor (not shown) for adjusting, i.e., advancing or withdrawing, an electrode. It should be noted that the present invention is described and shown with four micro-screws for individually adjusting four electrodes, although any number may be provided.

With particular reference to FIGS. 1A-1J, in one aspect of the present invention, an example of which is shown in, the device 100 is integrated onto a single or unitary base 104, such as a printed circuit (PC) board. In the illustrated embodiment, the base 104 is a double sided printed circuit board. The design of the printed circuit board 104 is such that it provides a base for all the components (see below).

In the illustrated embodiment, four drive screws 102A, 102B, 102C, 102D, which are typically 0-80 size or metric screws of a comparable size, are positioned parallel to one face (or surface) 104A of the printed circuit board 104. The head 108A, 108B, 108C, 108D of each screw 102A, 102B, 102C, 102D rests in a respective hole or aperture 106C, 106D of the circuit board 104. The holes 106A, 106B, 106C, 106D provide a shoulder to accurately locate the position of the respective screw 102A, 102B, 102C, 102D with the shaft 110A, 110B, 110C, 110D of each screw 102A, 102B, 102C, 102D flat against and guided by the circuit board 104. The screws 102A, 102B, 102C, 102D are held in place by a retaining bracket 112 just below the head 108, 108, 108, 108 of each screw 102A, 102B, 102C, 102D and respective stabilizing hooks 112A, 112B, 112C, 112D located in the shaft end of each screw 102A, 102B, 102C, 102D.

In the illustrated embodiment, the retaining bracket 113 is integral and mounted to the PC board 104 by one or more fasteners (not shown) inserted through bores 114. The stabilizing hooks 112A, 112B, 112C, 112D are affixed in respective holes or apertures 116A, 116B, 116C, 116D in the PC board 104. The retaining bracket 113, stabilizing hooks 112A, 112B, 112C, 112D and the hole-in-the-board are configured to hold the screws 102A, 102B, 102C, 102D securely in position, yet allow the screws 102A, 102B, 102C, 102D to turn freely.

A respective threaded shuttle 118A, 118B, 118C, 118D rides on each screw 102A, 102B, 102C, 102D. Like the screws 102A, 102B, 102C, 102D, the printed circuit board 104 provides guidance and a stable sliding surface for the shuttles 118A, 118B, 118C, 118D. The internal threads of the shuttles 118A, 118B, 118C, 118D couple with the threads of the screws 102A, 102B, 102C, 102D so as to move the shuttles 118A, 118B, 118C, 118D across the board 104 as the respective screw 102A, 102B, 102C, 102D is turned.

A flexible fused silica cannula 120A, 120B, 120C, 120D is secured in a groove 122 on a respective shuttle 118A, 118B, 118C, 118D with epoxy. The fused silica cannula 120A, 120B, 120C, 120D is guided by a hollow stationary stainless steel cannula 124 soldered on the printed circuit board 104. In the illustrated embodiment, only one stationary cannula 124 is shown, but it should be noted that any desired combination and position (one to four cannulae) and positioned along the printed circuit board 104 may be utilized.

In operation as a drive or micro-screw 102A, 102B, 102C, 102D is turned, the respective shuttle 118A, 118B, 118C, 118D moves up or down the shaft 110A, 110B, 110C, 110D of the screw 102A, 102B, 102C, 102D, which in turn pushes or pulls the flexible cannula 120A, 120B, 120C, 120D through the stationary cannula 124. The flexible cannula 120A, 120B, 120C, 120D carries an electrode bundle 126 which includes a plurality of wires 128, e.g., four wires. The electrode bundle 126 includes a first end 126A and a second end 126B. An electrode (not shown) is coupled to the second end 126B of the electrode bundle 126. The flexible cannulas 120A, 120B, 120C, 120D carry the electrode wires 128 with it allowing the electrode wires 128 to be moved precisely through the brain tissue.

The electrode wires 128 that feed into the flexible cannula 120A, 120B, 120C, 120D pass through the printed circuit board 104 and attach to a surface mount connector 130 on the reverse side 104B of the board 104 through connection holes 136.

Figure 2D:
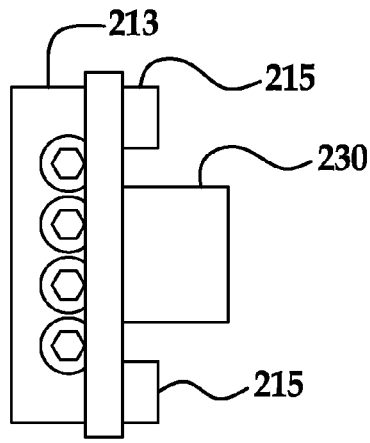
FIG. 2D is a first front view of the system of FIG. 2A.
Figure 2E:
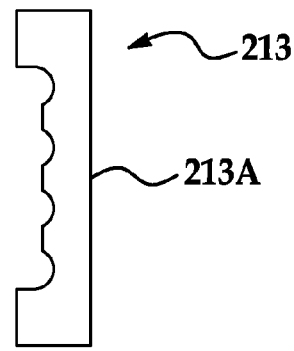
FIG. 2E is a second end view of a retaining bracket of the system of FIG. 2A.
Figure 2F:
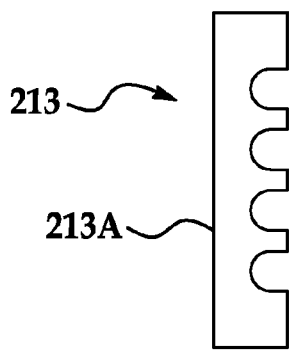
FIG. 2F is a first end view of the retaining bracket of the system of FIG. 2A.
Figure 2G:
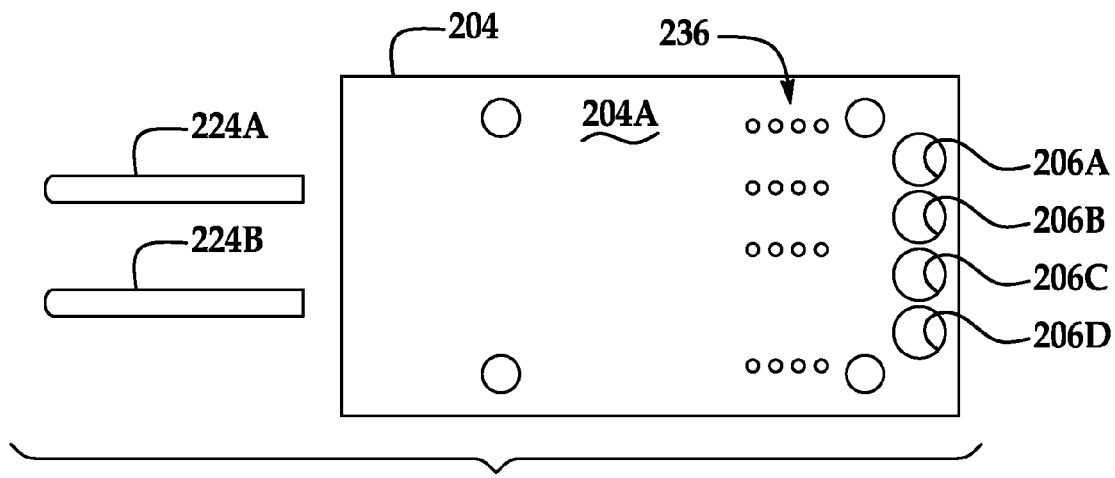
FIG. 2G is a component view of several components of the system of FIG. 2A.

A cover 132 may be attached to the top of the retainer bracket 113, protecting the exposed wires and moving parts. The cover 132 may be made of clear plastic or may have a number of viewing ports (as shown in FIG. 2B) and may be coupled to the board 104 using the fasteners 115 through bores 132A.

With particular reference to FIGS. 2A-2G, in an alternate embodiment in which like parts or numbered in a similar manner, one or more of the components of an integrated microdrive and electrode system or device, may be unitarily formed, e.g., out of plastic using an injection molding process. For example, in the illustrated embodiment, the board 204, a screw retainer 213 may be unitarily formed. An electrical connector 230 (or provisions for the mounting thereof), may also be included in the unitarily formed piece.

The screw retainer 213 replaces the retaining bracket 113 and the separate stabilizing hooks 112A, 112B, 112C, 112D of the first embodiment. The screw retainer 213 includes a first side 213A with a plurality of U-shaped apertures 214 through which the shafts 210 of the micro-screws 102 are inserted and which may form, along with the base 204, a shoulder for the heads 108A, 108B, 108C, 108D of the micro-screws 102. The opposite side of the screw retainer 213 (see FIG. 2E) retains the end of the micro-screw 102 opposite the head 108 in position.

A cover 232, which may also be injection molded, may also be provided. In one embodiment, the cover snaps onto the device or may be connected to the board 204, or the screw retainer 213 by a living hinge. The cover 232 may includes a plurality of viewing windows 232A (see FIG. 2A).

Additionally, in the alternative embodiment two stationery cannulae 224A, 224B are used. Each stationary cannula 224A, 224B is used to guide two sets of electrode bundles 226A & 226B, 226C & 226D.

With particular reference to FIGS. 3A-3K, in an alternate embodiment in which like parts or numbered in a similar manner, one or more of the components of an integrated micro drive and electrode system or device, may be unitarily formed, e.g., out of plastic using an injection molding process. For example, in the illustrated embodiment, the board 304 and a screw retainer may be unitarily formed. An electrical connector (or provisions for the mounting thereof), may also be included in the unitarily formed piece.

Figure 3A:
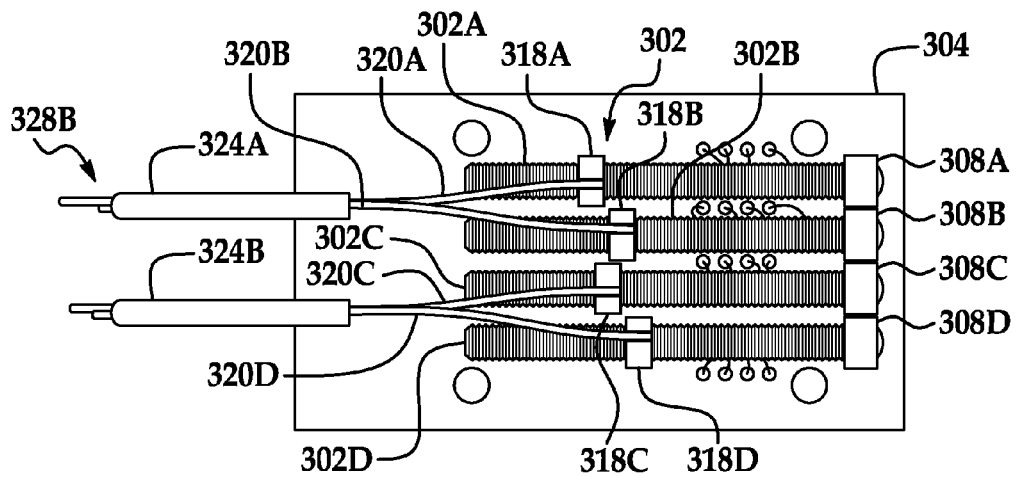
FIG. 3A is a top view of an integrated micro drive and electrode system, according to a third embodiment of the present invention.
Figure 3B:
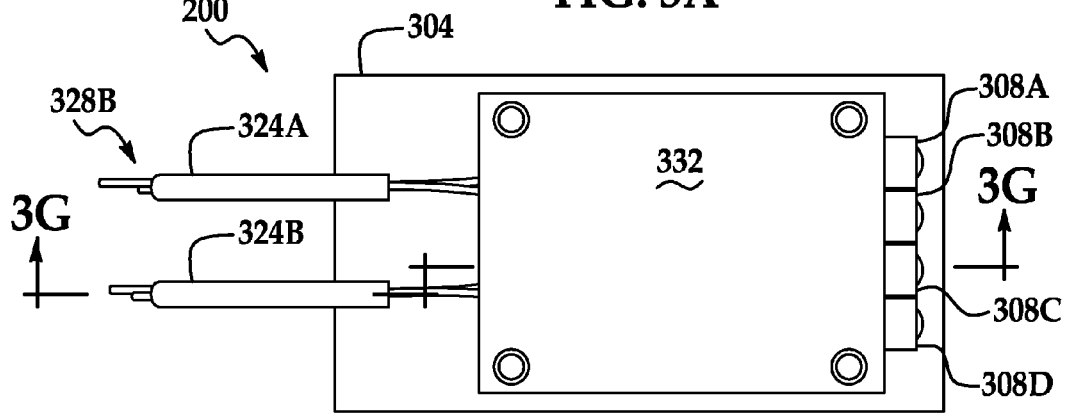
FIG. 3B is a second top view of the system of FIG. 3A.
Figure 3C:
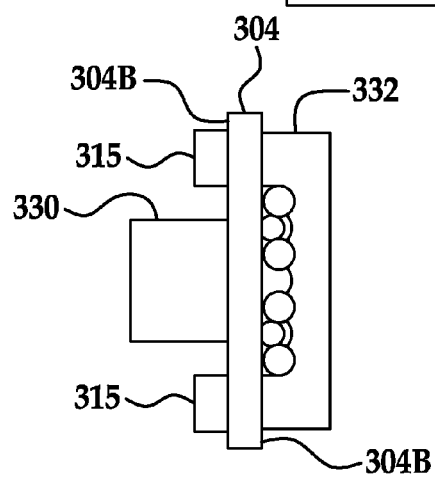
FIG. 3C is a second end view of the system of FIG. 3A.
Figure 3D:
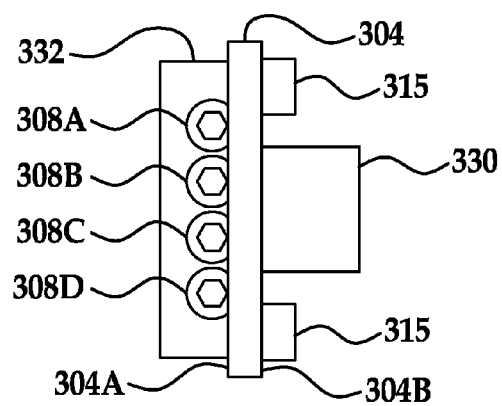
FIG. 3D is a first end view of the system of FIG. 3A.
Figure 3E:
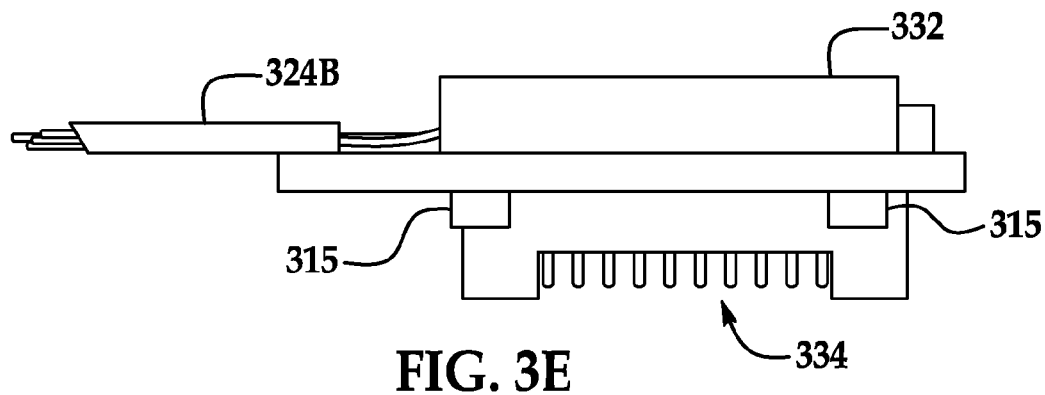
FIG. 3E is a side view of the system of FIG. 3A.
Figure 3F:
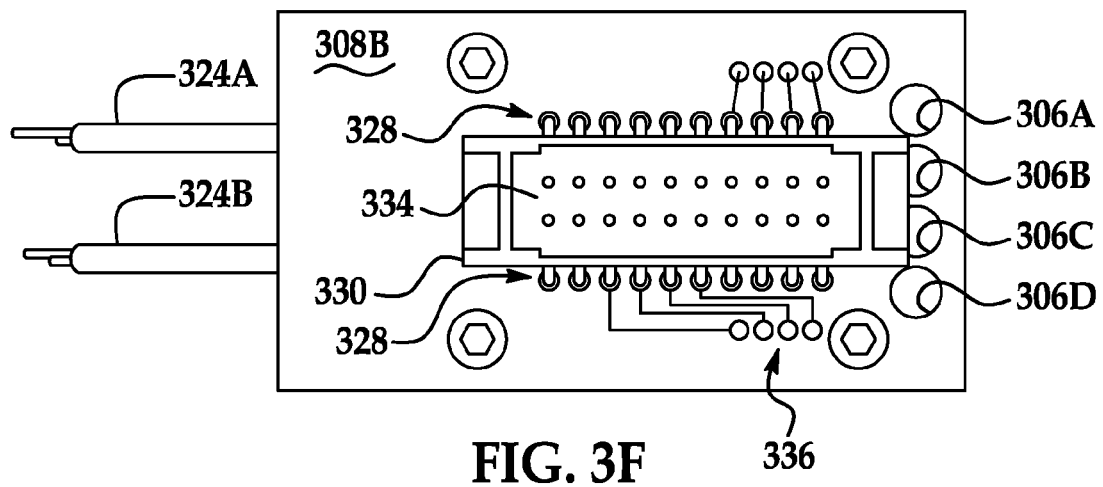
FIG. 3F is a bottom view of the system of FIG. 3A.
Figure 3G:
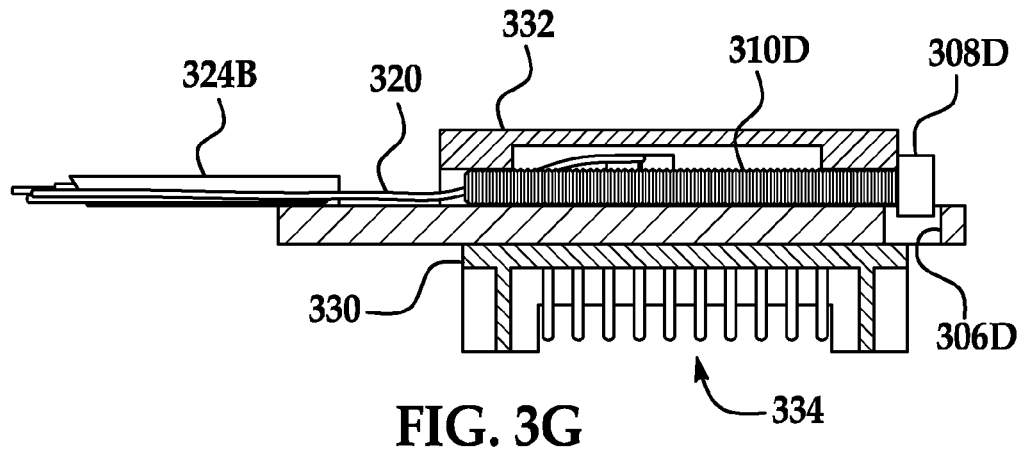
FIG. 3G is a cut-away view of the system of FIG. 3A.
Figure 3H:
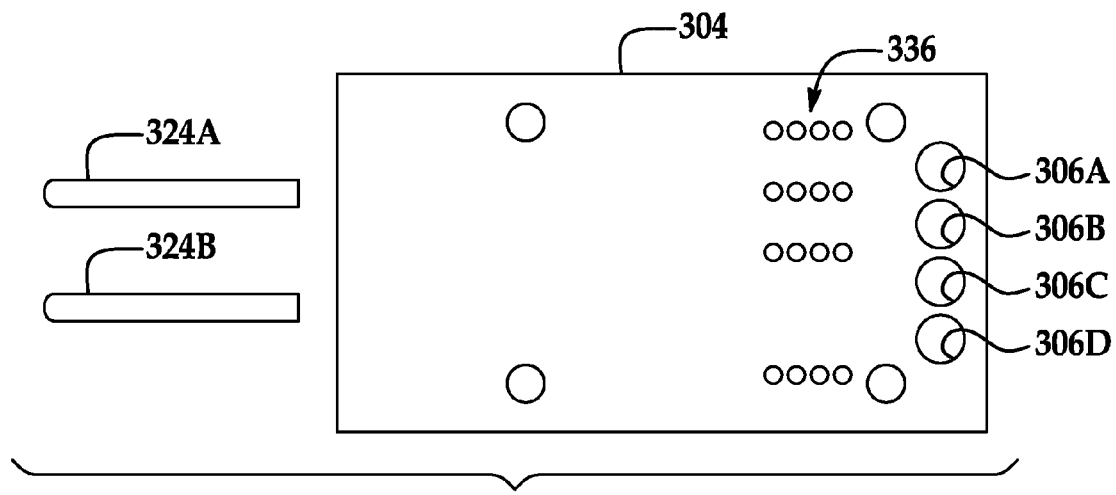
FIG. 3H is a component view of the system of FIG. 3A.
Figure 3I:
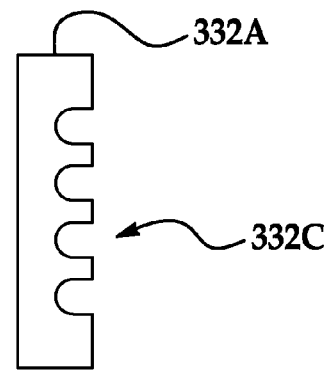
FIG. 3I is a first end view of an integrated cover and bracket of the system of FIG. 3A.
Figure 3J:
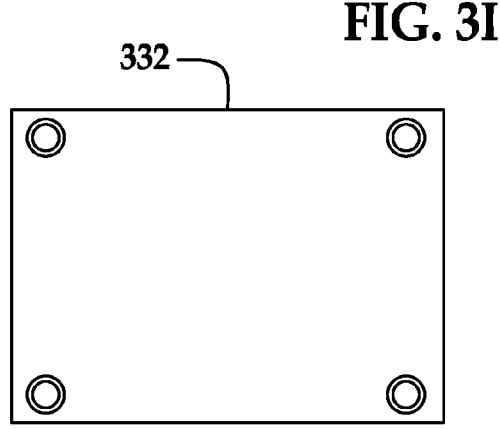
FIG. 3J is a top view of the integrated cover and bracket of FIG. 3I.
Figure 3K:
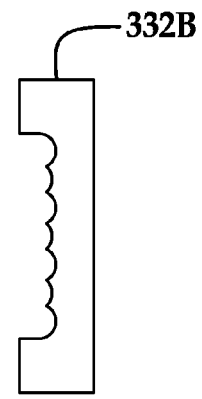
FIG. 3K is a second end view of the integrated cover and bracket of FIG. 3J.

In the illustrated embodiment, the cover 232 of the embodiment in FIGS. 2A-2G is replaced by an integrated cover/retainer 332 (see FIGS. 3I, 3J, 3K). The integrated cover/retainer 332 has a first end 332A which includes apertures 332C for positioning the heads 308A, 308B, 308C, 308D of the micro-screws 302 and a second end 332B which is used to maintain the position of the opposite end of the micro-screws 302. The integrated cover/retainer 332 may be made of clear plastic.

In operation, the device 100, 200, 300, allows a plurality of electrode bundles 126, 226, 336, e.g., but not limited to, 4, to be independently advanced or withdrawn in (brain tissue). The device 100, 200, 300, as described herein, utilizes simple mechanical parts mounted to a common board, such as a PC board, combining the mechanical and electrical micro-drive components into a single package. This provides a device 100, 200, 300 that is robust, easy to manufacture and to assemble, durable, and reusable. In addition, the device is inexpensive to manufacture and may be disposable.

Obviously, many modifications and variations of the present invention are possible in light of the above teachings.

What is claimed:

1. An apparatus, comprising:
   a unitarily formed base having a first end, a second end, a first surface, and an opposite second surface, each first and second surface being substantially planar and extending between the first end and the second end, the base including an aperture and a connection hole, the aperture and the connection hole extending through the base from the first surface to the second surface and orientated substantially perpendicular to the first surface;
   a micro-screw having a shaft that extends between a first end and a second end, the first end including a head that is positioned within the base aperture and defines a shoulder, the shaft being threaded and extending from the base first end towards the base second end;
   at least one retaining bracket mounted to the first surface of the base near the first end and adjacent to the base aperture, the at least one retaining bracket having an inner surface that defines an opening that is sized to receive the micro-screw therethrough such that the micro-screw is positioned between the retaining bracket inner surface and the base first surface, the micro-screw extending through bracket opening such that the shoulder rests against one side of the retaining bracket and an edge of the base aperture, the micro-screw being held along, and rotatable about, an axis parallel to the base, by the retaining bracket;
   a cannula having an internal bore and being mounted to the first surface;
   a shuttle having a bore with internal threads and an outer surface that is adjacent to the base first surface and is movable along the base first surface, the internal threads of the bore of the shuttle being in a coupling relationship with the threads of the micro-screw, the micro-screw being rotatable in a first rotary direction causing the shuttle to be advanced along the micro-screw in a first direction, the micro-screw being rotatable in a second rotary direction causing the shuttle to be advanced along the micro-screw in a second direction;
   an electrode having a first end and a second end and being coupled to the shuttle, the second end of the electrode being threaded through the cannula such that motion of the shuttle along the micro-screw moves the electrode through the cannula;

a surface mount connector mounted on the second surface of the base; and, an electrode wire electrically, one end of the electrode wire forming the electrode and another end of the electrode wire being electrically connected to the surface mount connector.

2. An apparatus, as set forth in claim 1, the base including a second aperture and a second connection hole, the second aperture and second connection hole extending through the base from the first surface to the second surface, the apparatus including:

a second micro-screw having a head and a shaft, the head of the second micro-screw being positioned within the second aperture and defining a shoulder which rests against the one side of the retaining bracket and an edge of the second aperture, the shaft of the second micro-screw being threaded and extending towards the second end, the second micro-screw being held along, and rotatable about, the axis parallel to the base, by the retaining bracket;

a second shuttle having a bore with internal threads, the internal threads of the bore of the second shuttle being in a coupling relationship with the threads of the second micro-screw, the second micro-screw being rotatable in the first rotary direction causing the second shuttle to be advanced along the second micro-screw in the first direction, the second micro-screw being rotatable in a second rotary direction causing the second shuttle to be advanced along the second micro-screw in the second direction;

a second electrode having a first end and a second end and being coupled to the second shuttle, the second end of the second electrode being threaded through the cannula such that motion of the second shuttle along the second micro-screw moves the second electrode through the cannula; and, a second electrode wire, one end of the electrode wire forming the second electrode and another end of the second electrode wire being electrically connected to the surface mount connector.

3. An apparatus, as set forth in claim 1, further comprising a flexible cannula secured within a groove defined along the shuttle outer surface, the electrode being secured within the flexible cannula.

4. An apparatus, as set forth in claim 1, wherein the retaining bracket is secured to the base by one or more fasteners.

5. An apparatus, as set forth in claim 1, wherein the retaining bracket is integral with the base.

6. An apparatus, as set forth in claim 1, wherein the first surface of the base provides a guide and a stable sliding surface for the shuttle.

7. An apparatus, as set forth in claim 1, the surface mount connector having at least one pin, the first end of the electrode being electrically connected to the pin.

8. An apparatus, as set forth in claim 1, further comprising a cover attached to a top of the retainer bracket.

9. An apparatus, as set forth in 8, wherein the base, retaining bracket and cover are unitarily formed and further comprising a living hinge coupling the base and the cover.

10. An apparatus, as set forth in claim 1, wherein the shaft second end includes an internal bore, the apparatus further includes a stabilizing hook fixed to the base and having a hook end extending into the internal bore of the end of the micro-screw to facilitate coupling the micro-screw to the base.

11. An apparatus, comprising:

a unitarily formed base having a first end, a second end, a first surface and a second surface, each first and second surface being substantially planar and extending between the first end and the second end, the base include first and second apertures and first and second connection holes, the first and second apertures and the first and second connection holes extending through the base from the first surface to the second surface and orientated substantially perpendicular to the first surface;

at least one retaining bracket mounted to the first surface of the base near the first end, the bracket being positioned over the first and second apertures, the at least one retaining bracket including a first side, a second side, and an inner surface that defines an opening that extends from the first side to the second side;

a first micro-screw having and a shaft that extends between a first end and a second end, the first end including a head that is positioned within the first aperture and defining a first shoulder which rests against the first side of the retaining bracket and an edge of the first aperture, the shaft of the first micro-screw being threaded and extending towards the base second end, the first micro-screw extending through the bracket opening such that the first micro-screw is orientated between the bracket and the base first surface, the first micro-screw being held along, and rotatable about, an axis parallel to the base, by the retaining bracket;

a first cannula having an internal bore and being mounted to the first surface;

a first shuttle having a bore with internal threads and outer surface that is adjacent to the base first surface and is movable along the base first surface, the internal threads of the bore of the shuttle being in a coupling relationship with the threads of the micro-screw, the micro-screw being rotatable in a first rotary direction causing the shuttle to be advanced along the micro-screw in a first direction, the micro-screw being rotatable in a second rotary direction causing the shuttle to be advanced along the micro-screw in a second direction;

a first electrode having a first end and a second end and being coupled to the shuttle, the second end of the first electrode being threaded through the first cannula such that motion of the first shuttle along the first micro-screw moves the electrode through the cannula;

a second micro-screw having a head and a shaft, the head of the second micro-screw being positioned within the second aperture and defining a second shoulder which rests against the first side of the retaining bracket and an edge of the second aperture, the shaft of the second micro-screw being threaded and extending towards the base second end, the second micro-screw being held along, and rotatable about, an axis parallel to the base, by the retaining bracket;

a second cannula having an internal bore and being mounted to the first surface;

a second shuttle having a bore with internal threads and outer surface that is adjacent to the base first surface and is movable along the base first surface, the internal threads of the bore of the second shuttle being in a coupling relationship with the threads of the second micro-screw, the second micro-screw being rotatable in the first rotary direction causing the second shuttle to be advanced along the second micro-screw in the first direction, the second micro-screw being rotatable in a second rotary direction causing the second shuttle to be advanced along the second micro-screw in the second direction;

a second electrode having a first end and a second end and being coupled to the second shuttle, the second end of the second electrode being threaded through the second cannula such that motion of the second shuttle along the second micro-screw moves the second electrode through the second cannula a surface mount connector mounted on the second surface of the base;

a first electrode wire, one end of the first electrode wire forming the first electrode and another end of the first electrode wire being electrically connected to the surface mount connector; and a second electrode wire, one end of the second electrode wire forming the second electrode and another end of the second electrode wire being electrically connected to the surface mount connector.

12. An apparatus, as set forth in claim 11, further comprising:

a first flexible cannula secured within a groove defined along the first shuttle outer surface, the first electrode being secured within the flexible cannula; and a second flexible cannula secured within a groove defined along the second shuttle outer surface, the second electrode being secured within the flexible cannula.

13. An apparatus, as set forth in claim 11, wherein the retaining bracket is secured to the base by one or more fasteners.

14. An apparatus, as set forth in claim 11, wherein the retaining bracket is integral with the base.

15. An apparatus, as set forth in claim 11, wherein the first surface of the base provides a guide and a stable sliding surface for the first and second shuttles.

16. An apparatus, as set forth in claim 11, the surface mount connector having first and second pins, the another end of the first and second electrode wires being electrically connected to the first and second pins, respectively.

17. An apparatus, as set forth in claim 11, further comprising a cover attached to a top of the retainer bracket.

18. An apparatus, as set forth in 17, wherein the retaining bracket and cover are unitarily formed.

19. An apparatus, as set forth in claim 1, wherein the base has a rectangular shape, the first and second surfaces of the base being contained within parallel planes.

20. An apparatus, as set forth in claim 19, wherein the base being comprised of a PC board.

21. An apparatus, as set forth in claim 11, wherein the base has a rectangular shape, the first and second surfaces of the base being contained within parallel planes.

22. An apparatus, as set forth in claim 21, where the base being comprised of a PC board.

23. An apparatus, as set forth in claim 1, further comprising:

a first retaining bracket positioned adjacent to the micro-screw first end; and a second retaining bracket positioned adjacent to the micro-screw second end.

24. An apparatus, as set forth in claim 11, further comprising:

a first retaining bracket positioned adjacent to the first micro-screw first end; and a second retaining bracket positioned adjacent to the first micro-screw second end.

* * * * *

UNITED STATES PATENT AND TRADEMARK OFFICE
CERTIFICATE OF CORRECTION

PATENT NO. : 8,428,680 B2  Page 1 of 1
APPLICATION NO. : 12/255223
DATED : April 23, 2013
INVENTOR(S) : J. Wayne Aldridge et al.

It is certified that error appears in the above-identified patent and that said Letters Patent is hereby corrected as shown below:

In the Claims

Column 8, line 18: Please delete "having and a shaft" and replace with -- having a shaft --.

Signed and Sealed this
Eighteenth Day of June, 2013

Teresa Stanek Rea
*Acting Director of the United States Patent and Trademark Office*